(12) United States Patent
Sindelar et al.

(10) Patent No.: US 8,779,120 B2
(45) Date of Patent: Jul. 15, 2014

(54) MACROCYCLIC DERIVATIVES OF GLYCOLURILS, AND METHODS OF PREPARING AND USING THE SAME

(75) Inventors: Vladimir Sindelar, Veverske Kninice (CZ); Jan Svec, Cerveny Kostelec (CZ); Vaclav Havel, Opava (CZ)

(73) Assignee: Masarykova Univerzita, Brno (CZ)

( * ) Notice: Subject to any disclaimer, the term of this patent is extended or adjusted under 35 U.S.C. 154(b) by 132 days.

(21) Appl. No.: 13/265,432

(22) PCT Filed: Oct. 26, 2010

(86) PCT No.: PCT/CZ2010/000110
§ 371 (c)(1),
(2), (4) Date: Oct. 20, 2011

(87) PCT Pub. No.: WO2011/057590
PCT Pub. Date: May 19, 2011

(65) Prior Publication Data
US 2012/0041192 A1  Feb. 16, 2012

(30) Foreign Application Priority Data

Nov. 16, 2009 (CZ) ................ PV 2009-761

(51) Int. Cl.
*C07D 487/22* (2006.01)
*C07D 487/14* (2006.01)

(52) U.S. Cl.
CPC .......... *C07D 487/14* (2013.01); *C07D 487/22* (2013.01)
USPC ...................... 540/460; 548/303.4

(58) Field of Classification Search
USPC ...................... 548/303.4; 540/460
See application file for complete search history.

(56) References Cited

U.S. PATENT DOCUMENTS 5,298,539 A    3/1994  Singh et al.

FOREIGN PATENT DOCUMENTS

| EP | 366884 A2 * | 5/1990 |
| EP | 1094065 | 4/2001 |
| WO | WO0068232 | 11/2000 |
| WO | WO2007106144 | 9/2007 |

OTHER PUBLICATIONS

Svec et al., Angewandte Chemie, International Edition (published online Mar. 9, 2010), 49(13), pp. 2378-2381.*

Lagona, J., et al., "The Cucurbit[n]uril Family", Angewandte Chemie, Int'l Edition, Wiley-Vch Verlag Gmbh & Co., Weinheim, vol. 44, No. 31, Aug. 5, 2005, pp. 4844-4870.
Svec, J., et al., "Bambus[6]uril**", Angewandte Chemie, Wiley-Vch Verlag GmbH & Co., Weinheim, vol. 122, No. 13, Mar. 9, 2010, pp. 2428-2431.
Freeman, W.A. et al., "Cucurbituril", J. Am. Chem. Soc. 1981, 103, 7367-7368.
Huang, Wei-Hao, et al., "Chiral Recognition inside a Chiral Cucurbituril**", Angew. Chem., Int. Ed. 2007, 46, 7425-7427.
Huang, Wei-Hao, et al., "Nor-Seco-Cucurbit[10]uril Exhibits Homotropic Allosterism", J. Am. soc 2006, 128, 14744-14745.
Isaacs, L., et al., "The Inverted Cucurbit[n]uril Family", J. Am Chem. Soc. 2005, 127, 18000-18001.
Kim, Jaheon, et al., "New Cucurbituril Homologues: Syntheses, Isolation, Characterization, and X-ray Crystal Structures . . . ", J. Am. Chem. Soc. 2000, 122, 540-541.
Lagona, Jason et al., "The Cucurbit[n]uril Family", Angew. Chem., Int. Ed. 2005, 44, 4844-4870.
Miyahara, Yuji et al., "Remarkably Facile Ring-Size Control in Macrocyclization: Synthesis of Hemicucurbit[6]uril and . . . ", Angew. Chem., Int. Ed. 2004, 43, 5019-5022.
Rebek, Julius, Jr., "Reversible Encapsultion and Its Consequences in Solution", Acc. Chem. Res. 1999, 32, 278-286.
Rowan, A.E., et al., "Molecular and Supramolecular Objects from Glycoluril", Acc. Chem. Res. 1999, 32, 995-1006.

* cited by examiner

*Primary Examiner* — Laura L. Stockton
(74) *Attorney, Agent, or Firm* — Notaro, Michalos & Zaccaria P.C.

(57) ABSTRACT

The present invention relates to novel macrocyclic derivatives of glycolurils of general formula I, and methods of their preparation. These novel derivatives can be used for the selective removing of various compounds from solutions in polar and nonpolar solvents, and from water, e.g. for water purification and desalination, also for separation of liquid mixtures and mixtures of gases and organic solvent vapors, preparation of ion-exchange materials and materials which are used as stationary phase in chromatography, construction of sensors, transport and targeting of drugs in organisms, and also preparation of materials bearing aromatic or curative compounds.

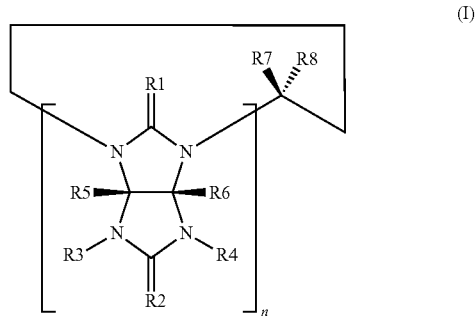

16 Claims, 4 Drawing Sheets

MACROCYCLIC DERIVATIVES OF GLYCOLURILS, AND METHODS OF PREPARING AND USING THE SAME

CROSS-REFERENCE TO RELATED APPLICATIONS

This application is a U.S. National Phase application entitled to the benefit of International Application PCT/CZ2010/000110, filed on Oct. 26, 2010, and also of Czech Republic Application PV 2009-761, filed on Nov. 16, 2009.

FIELD OF THE INVENTION

The present invention relates to novel macrocyclic derivatives of glycolurils, and methods of preparation and use thereof.

BACKGROUND ART

Glycoluril is a bicyclic molecule which is used for the preparation of supramolecular hosts, i.e. molecules that are able to bind other molecules (guests) through non-covalent interactions. There are several examples of glycoluril based supramolecular hosts. Nolte and co-workers described glycolurils terminated by xylylene units which are able to self-assembly into dimeric aggregates and/or to form host-guest complexes with small molecules (Rowan, A. E.; Elemans, J. A. A. W.; Nolte, R. J. M. *Acc. Chem. Res.* 1999, 995-1006). Rebek and co-workers prepared molecules, in which terminal glycoluril units are connected through various spacers. These molecules are able to self-associate in non-polar solvents into spherical structures. These structures are stabilized by N—H . . . O hydrogen bonds which are formed between terminal glycoluril units (Rebek, J., Jr. *Acc. Chem. Res.* 1999, 32, 278-286). Singh et al. (U.S. Pat. No. 5,298,539 to Cytec Industries) describes additives for improving tire cord adhesion and toughness of vulcanized rubber compositions, containing linear oligomers of glycoluril units connected directly by N—N bond.

Among the glycoluril based supramolecular hosts, most attention is paid to cyclic glycoluril oligomers called cucurbit[n]urils in which n glycoluril units are connected through 2n methylene bridges (Lagona, J.; Mukhopadhyay, P.; Chakrabarti, S.; Isaacs, L. *Angew. Chem., Int. Ed.* 2005, 44, 4844-4870). Cucurbit[6]uril, the first member of the cucurbituril family, was prepared in 1905 (Behrend, R; Meyer, E; Rusche, F. *Liebigs Ann. Chem.* 1905, 339), but its macrocyclic structure was not discovered until 1981 (Freeman, W. A.; Mock, W. L.; Shih, N.-Y. *J. Am. Chem. Soc.* 1981, 103, 7367). In the beginning of the 21$^{st}$ century two research groups led by K. Kim and A. Day independently described the preparation and isolation of cucurbit[n]urils in which the number of glycoluril units n varies in the range from 5 to 10 (A. I. Day, A. P. Arnold, R. J. Blanch (Unisearch Limited, Australia), WO2000068232. Day, A.; Arnold A. P.; Blanch, R. J.; Snushall, B. *J. Org. Chem.* 2001, 66, 8094. K. Kim, J. Kim, I.-S. Jung, S.-Y. Kim, E. Lee, J.-K. Kang (Postech Foundation, South Korea), EP1094065. Kim, J.; Jung, I.-S.; Kim, S. Y.; Lee, E.; Kang, J.-L.; Sakamoto, S.; Yamaguchi, K.; Kim, K. *J. Am. Chem. Soc.* 2000, 122, 540). Recently it was also demonstrated that the choice of suitable reaction conditions allows for the preparation of CB analogs such as diastereomeric inverted cucurbit[n]urils (Isaacs, L.; Park, S.-K.; Liu, S.; Ko, Y. H.; Selvapalam, N.; Kim, Y.; Kim, H.; Zavalij, P. Y.; Kim, G.-H.; Lee, H.-S.; Kim, K. *J. Am. Chem. Soc.* 2005, 127, 18000-18001.), bis-ns cucurbit[10]uril (Huang, W.-H.; Liu, S.; Zavalij, P. Y.; Isaacs, L. *J. Am. Chem. Soc.* 2006, 128, 14744-14745), and/or (±)-bis-ns-cucurbit[6]uril (Huang, W.-H.; Zavalij, P. Y.; Isaacs, L. *Angew. Chem., Int. Ed.* 2007, 46, 7425-7427). Using the same approach, Isaac's group has been able to isolate acyclic oligomers with the number of glycoluril units ranging from 2 to 6 (Huang, W.-H.; Zavalij, P. Y.; Isaacs, L. *J. Am. Chem. Soc.* 2008, 130, 8446-8454). Based on the size of its cavity, cucurbit[n]urils are able to form inclusion or exclusion complexes with organic and inorganic guests of various sizes. The binding is selective and the formed supramolecular complexes are characterized by high binding constants. These outstanding properties of cucurbit[n]urils have led to their use in a number of applications including waste stream remediation, controlled drug release, catalysis, sensors, and chromatography.

Cucurbit[n]urils are prepared by acid-catalyzed condensation between glycoluril and formaldehyde. Reaction is carried out in a concentrated mineral acid such as HCl and $H_2SO_4$ at temperature above 50° C. (e.g., WO0068232, WO2007106144). The separation of single cucurbit[n]uril homologues from the reaction mixture is time consuming and it is achieved by the combination of fractional crystallization and chromatography techniques. Another limit in cucurbit[n]urils applications is their insolubility in organic solvent. Also the solubility of cucurbit[n]urils in water is low, but it increases in the presence of metal or organic cations. Due to their rigid structure cucurbit[n]uril macrocycles are very difficult to modify.

In 2004 the preparation of new macrocyclic compounds based on ethyleneurea and formaldehyde were published (Miyahara, Y.; Goto, K.; Oka, M.; Inazu, T. *Angew. Chem., Int. Ed.* 2004, 43, 5019-5022). The structure of this macrocycle resembles the structure of cucurbit[n]uril which is cut in half along the equator. Therefore the authors named these new compounds hemicucurbit[n]urils (wherein n=6 and 12). In contrast to cucurbit[n]urils, hemicucurbit[n]urils are soluble in non-polar solvents. However they are capable of forming complexes with a limited range of anions, and these complexes have a relatively low association constant.

As we described above, macrocyclic molecules based on glycoluril are promising compounds which can act as supramolecular hosts. Low solubility and limited modifiability represent basic drawback for their further application.

New class of glycoluril based compounds which eliminates the disadvantages of known glycoluril macrocyclic compounds is the object of the present invention.

DISCLOSURE OF THE INVENTION

Object of the present invention is a novel class of macrocyclic compounds of general formula I

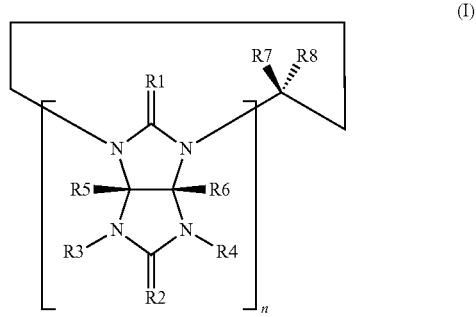

wherein n is an integer in the range of 4 to 24,

R1 and R2 are each independently O or S,

R3, R4, R7, R8 are each selected independently from the group consisting of hydrogen atom, alkyl, alkenyl, alkynyl, cycloalkyl, cycloalkenyl, aryl, heteroaryl, R5, R6 are each selected independently from the group consisting of hydrogen atom, —OH, —COOH, —NH$_2$, —NO$_2$, —NHNH$_2$, nitrile, alkyl, alkenyl, alkynyl, cycloalkyl, cycloalkenyl, alkoxy, hydrocarbylthio, hydrocarbylamino, dihydrocarbylamino, carboxyl, aryl, heteroaryl, wherein alkyl is a linear or branched alkyl chain having 1 to 30 carbon atoms, preferably $C_1$ to $C_{10}$, more preferably $C_1$ to $C_6$, and in which any of the —CH$_2$— groups can be replaced by —O—, —S— or —NH— group, while the alkyl can be unsubstituted or substituted by 1 to 5 groups selected from the group consisting of —OH, —SH, =O, halogen, aryl, —NH$_2$, —COOR$^c$, wherein R$^c$ is hydrogen atom or alkyl group having 1 to 6 carbon atoms, alkenyl is linear or branched chain containing 2 to 30 carbon atoms, preferably $C_2$ to $C_{10}$, more preferably $C_2$ to $C_6$, and containing at least one double bond, and in which any of the —CH$_2$— groups can be replaced by —O—, —S— or —NH— group, and any =CH— group can be replaced by =N—, while the alkenyl can be unsubstituted or substituted by 1 to 5 groups selected from the group consisting of —OH, —SH, =O, halogen, aryl, —NH$_2$, —COOR$^c$, where R$^c$ is hydrogen atom or alkyl group having 1 to 6 carbon atoms, alkynyl is linear or branched chain having 2 to 30 carbon atoms, preferably $C_2$ to $C_{10}$, more preferably $C_2$ to $C_6$, and containing at least one triple bond, and which can contain also a double bond, in this alkynyl chain any of the —CH$_2$— groups can be replaced by —O—, —S— or —NH— group, and any =CH— group can be replaced by =N—, while the alkynyl can be unsubstituted or substituted by 1 to 5 groups selected from the group consisting of —OH, —SH, =O, halogen, aryl, —NH$_2$, —COOR$^c$, where R$^c$ is hydrogen atom or alkyl group having 1 to 6 carbon atoms, cycloalkyl is linear or branched group having 3 to 10 carbon atoms, preferably $C_4$ to $C_8$, more preferably $C_5$ to $C_7$, and containing at least one cycle, in which any of the —CH$_2$— groups can be replaced by —O—, —S— or —NH— group, while the cycloalkyl can be unsubstituted or substituted by 1 to 5 groups consisting of —OH, —SH, =O, halogen, aryl, —NH$_2$, —COOR$^c$, where R$^c$ is hydrogen atom or alkyl group having 1 to 6 carbon atoms, cycloalkenyl is linear or branched group having 3 to 10 carbon atoms, preferably $C_4$ to $C_{10}$, more preferably $C_4$ to $C_8$, and containing at least one double bond and at least one cycle, in which any of the —CH$_2$— groups can be replaced by —O—, —S— or —NH— group, and any =CH— group can be replaced by =N—, while the cycloalkenyl can be unsubstituted or substituted by 1 to 5 groups consisting of —OH, —SH, =O, halogen, aryl, —NH$_2$, —COOR$^c$, where R$^c$ is hydrogen atom or alkyl group having 1 to 6 carbon atoms, alkoxy is a group —OR$^a$, where R$^a$ is selected from the group consisting of alkyl, alkenyl, alkynyl, cycloalkyl, cycloalkenyl, as defined above, hydrocarbylthio is a group —SR$^a$, where R$^a$ is selected from the group consisting of alkyl, alkenyl, alkynyl, cycloalkyl, cycloalkenyl, as defined above, hydrocarbylamino is a group —NHR$^a$, where R$^a$ is selected from the group consisting of alkyl, alkenyl, alkynyl, cycloalkyl, cycloalkenyl, as defined above, dihydrocarbylamino is a group NR$^a$R$^b$, where R$^a$ and R$^b$ are each independently selected from the groups consisting of alkyl, alkenyl, alkynyl, cycloalkyl, cycloalkenyl, as defined above, carboxyl is a group —COOR$^a$, where R$^a$ is selected from the group consisting of alkyl, alkenyl, alkynyl, cycloalkyl, cycloalkenyl, as defined above, aryl is a hydrocarbon group having 6 to 30 carbon atoms, preferably 6 to 10 carbon atoms, and containing at least one aromatic ring, and the aryl can be unsubstituted or substituted by 1 to 5 groups selected independently from the group consisting of —OH, —SH, =O, halogen, —NH$_2$, —COOR$^c$, where R$^c$ is hydrogen atom or alkyl group having 1 to 6 carbon atoms. Preferably, aryl is selected from the group consisting of phenyl, benzyl, naphthyl, each of them unsubstituted or substituted by 1 to 5 groups selected independently from —OH, —SH, =O, halogen, aryl, —NH$_2$, —COOR$^c$, heteroaryl is a hydrocarbon group having 4 to 30 carbon atoms, preferably 4 to 10 carbon atoms, and containing at least one aromatic ring, containing at least one heteroatom, preferably one or two heteroatoms selected from the group comprising O, S, N, and the heteroaryl can be unsubstituted or substituted by 1 to 5 groups selected independently from —OH, —SH, =O, halogen, aryl, —NH$_2$, —COOR$^c$, where R$^c$ is hydrogen atom or alkyl group having 1 to 6 carbon atoms.

Halogen atoms are selected from the group consisting of —F, —Cl, —Br, —I.

It is further an object of the present invention to provide a method of preparing macrocyclic compounds of general formula I by reacting glycoluril derivatives of general formula II,

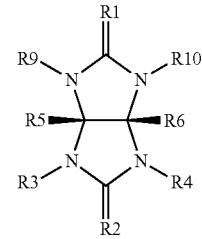

(II)

wherein

R1, R2 are independently O or S,

R3, R4 are each selected independently from the group consisting of alkyl, alkenyl, alkynyl, cycloalkyl, cycloalkenyl, aryl, heteroaryl, R5 and R6 are each selected independently from the group consisting of hydrogen atom, —OH, —COOH, —NH$_2$, —NO$_2$, —NHNH$_2$, nitrile, alkyl, alkenyl, alkynyl, cycloalkyl, cycloalkenyl, alkoxy, hydrocarbylthio, hydrocarbylamino, dihydrocarbylamino, carboxyl, aryl, heteroaryl, R9 and R10 are each independently selected from the group consisting of —H, —Cl, —Br, —I, —CH$_2$OH, —CO-alkyl, —CO-aryl, —CH$_2$O-alkyl, —CH$_2$O-aryl, —CH$_2$SH, —CH$_2$S-alkyl, —CH$_2$S-aryl, provided that R3 and R4 do not have the meaning listed here for R9 and R10, with carbonyl compounds of general formula III or IV,

wherein R7 and R8 are each selected independently from the group consisting of hydrogen atom, alkyl, alkenyl, alkynyl, cycloalkyl, cycloalkenyl, aryl, heteroaryl, and m is an integer in the range of from 4 to 20.

The reaction between the compound of general formula II and the compound of general formula III or IV is carried out in the presence of an acid, which is preferably a mineral acid such as HF, HCl, HBr, HI, $H_2SO_4$, $H_3PO_4$, $HNO_3$, or an organic acid such as trifluoroacetic acid, methanesulfonic acid, or p-toluenesulfonic acid.

Nonpolar or polar solvents such as chloroform, dichloromethane, acetonitrile, tetrahydrofuran, toluene, ethyl acetate can be used, but are not necessary.

Another method of preparing the macrocyclic compounds of general formula I, wherein R7 and R8 are hydrogen atom, includes treating glycoluril derivatives of general formula IIa,

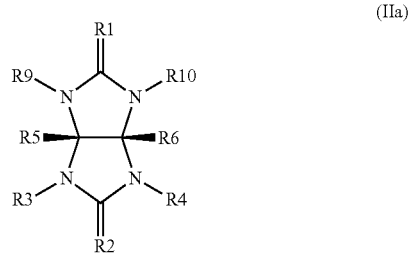

wherein
R1, R2 are independently O or S,
R3, R4 are each selected independently from the group consisting of alkyl, alkenyl, alkynyl, cycloalkyl, cycloalkenyl, aryl, heteroaryl,
R5 and R6 are each selected independently from the group consisting of hydrogen atom, —OH, —COOH, —$NH_2$, —$NO_2$, —$NHNH_2$, nitrile, alkyl, alkenyl, alkynyl, cycloalkyl, cycloalkenyl, alkoxy, hydrocarbylthio, hydrocarbylamino, dihydrocarbylamino, carboxyl, aryl, heteroaryl,
R9 and R10 are selected from the group consisting of —$CH_2OH$, —$CH_2O$-alkyl, —$CH_2O$-aryl, —$CH_2SH$, —$CH_2S$-alkyl, —$CH_2S$-aryl,
provided that R3 and R4 do not have the meaning listed here for R9 and R10, with an acid. Nonpolar or polar solvents can be used, but are not necessary.

Templating compounds may be used in both methods of preparation to increase the yield of the reaction and also to affect the number of glycoluril units in the macrocycle. Compounds suitable for the template synthesis are preferably selected from the group comprising anions such as $F^-$, $Cl^-$, $Br^-$, $I^-$, $PF_6^-$, $BF_4^-$, $CH3COO-$, $Ph-COO-$, and cations such as $Na^+$, $K^+$, $Cs^+$, $Ni^{2+}$. The macrocyclic compound precipitates from the solution during the reaction. The precipitate is preferably collected by filtration and it can be purified by any purification method commonly used in the field, e.g., recrystallization, chromatography and others. Macrocycles remaining in the solution can be precipitated from the solution by addition of a suitable solvent, e.g., acetone, isopropanol. Solid macrocycle can also be obtained by solvent evaporation.

The structure of the macrocycles can be further modified by additional reactions on the macrocycle. For example at least one of R1 and R2 can be transformed from O to S by treatment of the macrocycle (where R1 is O) with Lawesson reagents or related reagents. The substituents R3, R4, R5, R6, R7 and R8 can be converted into other substituents by reactions commonly known in the art.

The macrocyclic compounds of formula I wherein R3 and/or R4 are hydrogen atom can be obtained by hydrogenation of compounds of formula I wherein R3 and/or R4 are substituents removable by hydrogenation agents, such as benzyl. Hydrogenation agents commonly known in the art can be used.

The present invention thus covers a new class of macrocyclic compounds which was named bambus[n]urils (wherein n is ranging from 4 to 24) by the authors. In contrast to cucurbit[n]urils where n glycoluril units are connected through 2n methylene bridges there are just n glycoluril units connected through n methylene bridges in the bambus[n]uril macrocycle. Moreover, the smallest cucurbit[n]uril ever isolated is the macrocycle containing five glycoluril units (n=5). Due to the flexible structure bambus[n]urils are able to form a cycle containing only four glycoluril units (n=4). In contrast to cucurbit[n]urils which are not soluble in organic solvents, bambus[n]urils have shown good solubility in organic solvents including chloroform, methanol, dimethylsulfoxide or mixtures of these solvents. The solubility of bambus[n]urils can be influenced by the type of substitution particularly on R1, R2, R3, and R4 position. Considerable conformational changes in the macrocycle can be achieved by different substitution in positions R5 and R6. Depending on the size and character of the substituent R5 and R6 the glycoluril units change their orientation within the macrocycles and the macrocycles can accommodate various conformations. As a result the substituents R5 and R6 are included within the cavity of bambus[n]urils or located outside the macrocycle. The macrocycle modified by suitable functional groups, which are known in the art, can be attached to silica, polymer or metal surface.

The internal diameter of the bambus[n]uril cavity ranges from 0.3 to 1.8 nm. Because of their flexible structure, bambus[n]urils can adopt various sizes of the internal cavity as well as the portal. This allows to the macrocycle to form supramolecular complexes with various guest molecules including anions such as $F^-$, $Cl^-$, $Br^-$, $I^-$, $PF_6^-$, $PF_4^-$, $BF_4^-$, $CN^-$, $SCN^-$, $PO_4^{-3}$, $NO_3^-$, $CH_3COO^-$, $Ph-COO^-$, $CH_3-SO_3^-$, $Ph-SO_3^-$ and others, cations such as $K^+$, $Na^+$, $Cu^{2+}$, $Ni^{2+}$, $Cd^{2+}$, $Pb^{2+}$ and others and also neutral molecules such as methanol, ethanol, propanol, butanol, $CO_2$, CO, and others. Bambus[n]urils can also act as ditopic receptors which are able to bind simultaneously anion and cation. The ion or the compound which is bound to the bambus[n]urils can be selectively removed from the macrocycle by the treatment of the complex with peroxides, or by electrochemical and photochemical methods. For its ability to bind compounds listed above the macrocyclic compounds of general formula I may be used for selective removal of these compounds from polar and non-polar organic solvents and from water, e.g. purification of waste water or desalination. Water can be purified by bambus[n]urils in powder form or bambus[n]urils can be incorporated as nanoadditive into polymeric membranes. Polymeric membranes containing bambus[n]urils can be also used for the separation of liquid mixtures, and mixtures of gases and organic solvent vapors using the pervaporation, permeation, and sorption techniques. The macrocycles in which at least one of the groups R1 and R2 is S can be attached to a metal surface through a non-covalent interaction. Bambus[n]urils can be also covalently attached to the silica, alumina or polymer support through R1, R2, R3, R4, R5, or R6 bearing functional groups including —OH, —SH or —COOH. These bambus[n]uril-modified materials can be used as stationary phase in chromatography. For their ability to selectively bind some anions and cations bambus[n]urils can be used as a ion-exchange materials. Bambus[n]urils can be also used for the preparation of sensors for anion and cation detection and for the extraction, transportation, and regulation of an anion. Because of the ability to bind various compounds bambus[n]urils may be used for drug transportation and targeting in organisms, or in food and pharmaceutical industry as a matrix bearing aromatic or curative compounds.

A further object of the present invention is therefore the use of the macrocyclic compounds of general formula I comprising the formation of non-covalent bonds between macrocyclic compounds of general formula I and ions or neutral compounds. Especially it can be used for water purification, desalination, removal of various ions and/or compounds from the solution, separation of liquid mixtures and mixtures of gases and organic solvent vapors, preparation of ion-exchange materials and materials which are used as stationary phase in chromatography, the construction of sensors, the transportation and targeting of drugs in organisms, and also the preparation of materials bearing aromatic or curative compounds.

EXAMPLES OF CARRYING OUT THE INVENTION

Methods:
NMR spectroscopy was carried our on Bruker Avance 300 spectrometer in the mixture of deutero dimethyl sulfoxide and deuterochloroform d6-DMSO:CDCl$_3$=1:1, or in the mixture of deutero methanol and deuterochloroform CD$_3$OD: CDCl$_3$=2:1. Chemical shifts are shown in ppm. $^1$H NMR spectra were measured at the frequence of 300.13 MHz and referenced to chloroform signal 7.6 ppm, $^{13}$C NMR spectra were measured at the frequence of 75.77 MHz and referenced to CDCl$_3$ signal 77.0 ppm. MALDI-TOF mass spectra were obtained on Ultraflex III spectrometer. ESI-MS mass spectra were obtained on Agilent 6224 Accurate-Mass Time-of-Flight spectrometer. Diffraction data were obtained on KUMA KM-4 κ-axis CCD diffractometer with Mo—Kα radiation (λ=0.071073 nm). The temperature at which the measurements were performed was −153.15(2)° C. (120(2) K).

Example 1

Figure 1:
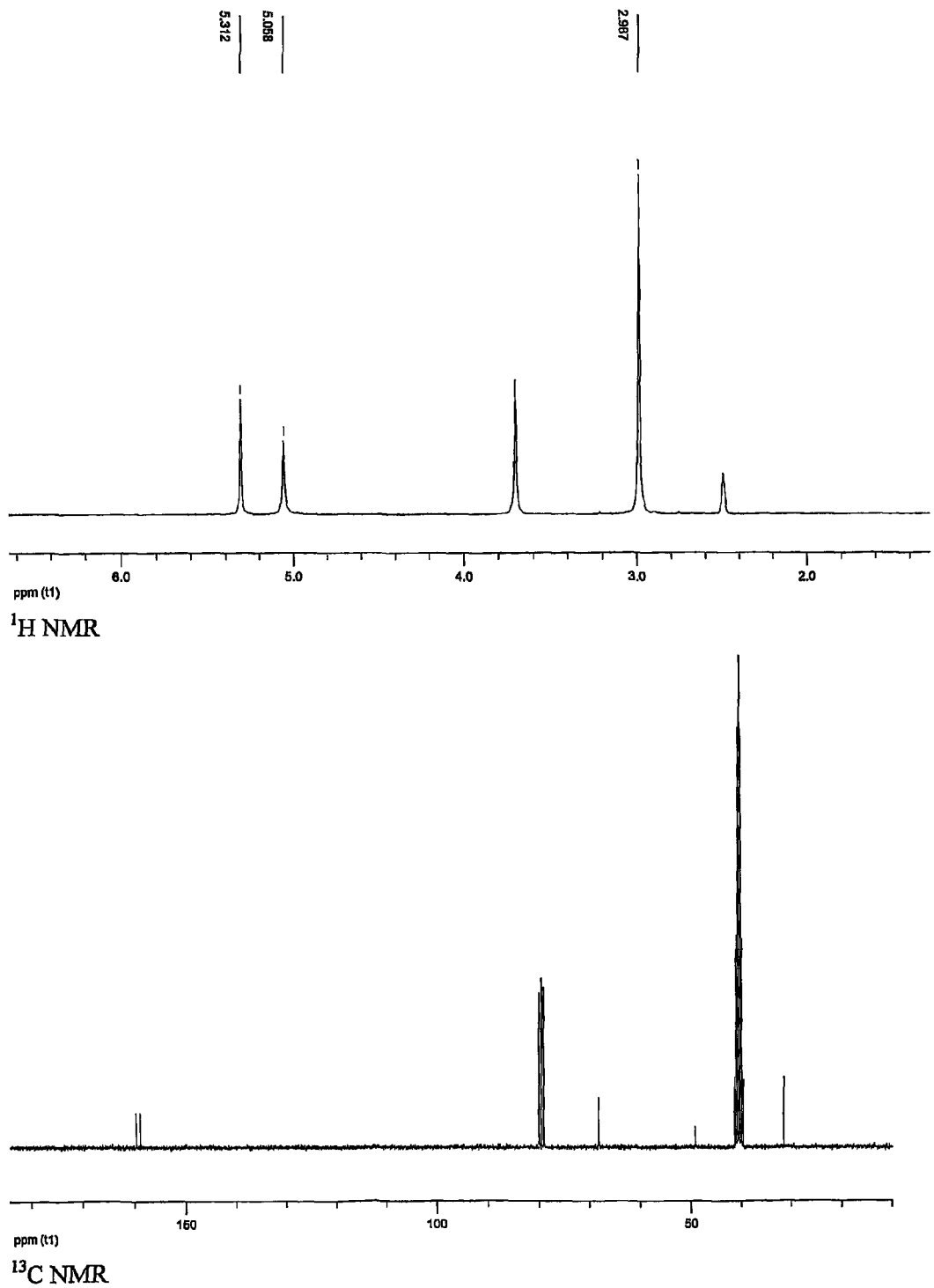
FIG. 1 shows the $^1$H and $^{13}$C NMR spectra of the macrocycle (M1) from Example 1.
Figure 2:
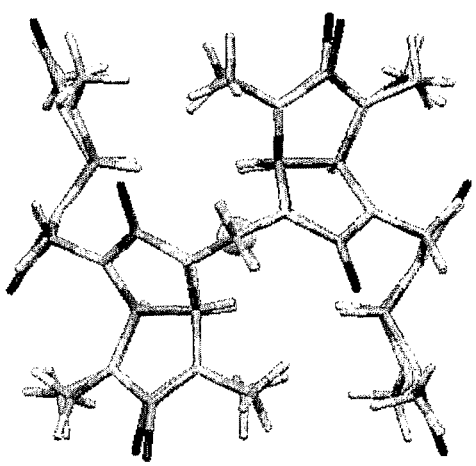
FIG. 2 shows the x-ray crystal structure of the complex between the macrocycle (M1) and chloride anion from Example 1. Solvent molecules and tetrabutylammonium cation were removed for clarity.
Figure 3:
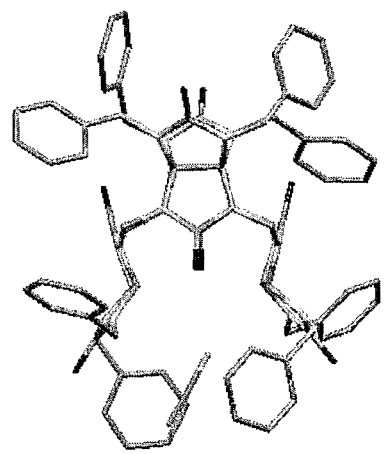
FIG. 3 shows the x-ray crystal structure of the macrocycle (M6) from Example 9. Hydrogen atoms and solvent molecules were removed for clarity.
Figure 4:
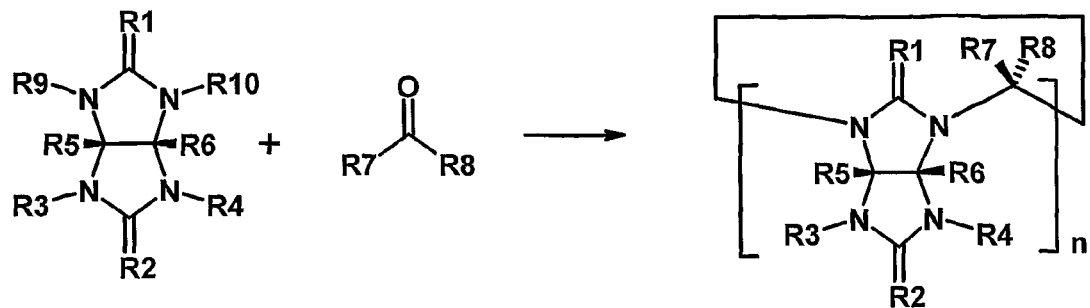
FIG. 4 shows the reaction scheme of the synthesis of the macrocyclic compounds of general formula I.

Dodecamethylbambus[6]uril (M1) (n=6; R1 and R2=O; R5, R6, R7, R8, R9, R10=H; R3, R4=methyl; for reaction scheme see FIG. 4)

2,4-dimethylglycoluril (9 g, 53 mmol) (the preparation published in Grillon, E.; Gallo, R.; Pierrot, M.; Boileau, J.; Wimmer, E. *Tetrahedron Lett.*, 1988, 29, 1015-1016) and paraformaldehyde (1.6 g, 53 mmol) were heated at 45° C. in HCl (5.4 M, 30 ml) until the starting material had dissolved completely. The solution was then allowed to cool down and was stirred at room temperature for 24 h. The resulting precipitate was collected by filtration, washed with concentrated HCl and water, and dried under vacuum to give white solid in 30% yield. $^1$H NMR (500 MHz, [D$_6$]DMSO:CDCl$_3$=1:1, 30° C., TMS): δ=5.51 (s, 12H, CH); 5.27 (s, 12H, CH$_2$); 3.20 ppm (s, 36H, CH$_3$); $^{13}$C NMR (125 MHz, [D$_6$]DMSO:CDCl$_3$=1:1, 30° C., TMS): δ=159.7, 158.9, 68.3, 49.2, 31.47 ppm; m.p.>300° C. (dec.); HRMS (ESI$^-$) m/z calcd for [C42H60N24O12+Cl$^-$]: 1127.4506; found: 1127.4462.

Example 2

Dodecamethylbambus[6]uril (M1) (n=6; R1 and R2=O; R5, R6, R7, R8, R9, R10=H; R3, R4=methyl; for reaction scheme see FIG. 4)

2,4-dimethylglycoluril (9 g, 53 mmol) and paraformaldehyde (1.6 g, 53 mmol) were heated at 90° C. in HCl (5.4 M, 30 ml) for 45 minutes. The resulting solid precipitated from the solution after standing for 6 h at room temperature. The precipitate was collected by filtration, washed with concentrated HCl and water, and dried under vacuum to give white solid in 26% yield. $^1$H NMR (500 MHz, [D$_6$]DMSO: CDCl$_3$=1:1, 30° C., TMS): δ=5.51 (s, 12H, CH); 5.27 (s, 12H, CH$_2$); 3.20 ppm (s, 36H, CH$_3$); $^{13}$C NMR (125 MHz, [D$_6$] DMSO:CDCl$_3$=1:1, 30° C., TMS): δ=159.7, 158.9, 68.3, 49.2, 31.47 ppm; m.p.>300° C. (dec.);
HRMS (ESI$^-$) m/z calcd for [C42H60N24O12+Cl$^-$]: 1127.4506; found: 1127.4481.

Example 3

Dodecamethylbambus[6]uril (M1) (n=6; R1 and R2=O; R5, R6, R7, R8, R9, R10=H; R3, R4=methyl; for reaction scheme see FIG. 4)

2,4-dimethylglycoluril (1.5 g, 8.5 mmol), paraformaldehyde (0.26 g, 8.5 mmol), and KCl (0.33 g, 4 mmol) were heated at 40° C. in the mixture of sulfuric acid (96%, 1 ml) and water (5 ml). for 36 h. The resulting precipitate was collected by filtration, washed with concentrated HCl and water, and dried under vacuum to give white solid in 21% yield. $^1$H NMR (500 MHz, [D$_6$]DMSO:CDCl$_3$=1:1, 30° C., TMS): δ=5.51 (s, 12H, CH); 5.27 (s, 12H, CH$_2$); 3.20 ppm (s, 36H, CH$_3$); $^{13}$C NMR (125 MHz, [D$_6$]DMSO:CDCl$_3$=1:1, 30° C., TMS): δ=159.7, 158.9, 68.3, 49.2, 31.47 ppm; m.p.>300° C. (dec.); HRMS (ESI⁻) m/z calcd for [C42H60N24O12+Cl⁻]: 1127.4506; found: 1127.4508.

Example 4

Dodecamethylbambus[6]uril (M1) (n=6; R1 and R2=O; R5, R6, R7, R8, R9, R10=H; R3, R4=methyl; for reaction scheme see FIG. 4)

2,4-dimethylglycoluril (1.5 g, 8.5 mmol), paraformaldehyde (0.26 g, 8.5 mmol), and KCl (0.33 g, 4 mmol) were heated at room temperature in the mixture of sulfuric acid (96%, 1 ml) and water (5 ml). for 48 h. The resulting precipitate was collected by filtration. White powder was dissolved in mixture of methanol:chloroform=1:1 and purified using GPC (gel permeation chromatography). Yield 21%. $^1$H NMR (500 MHz, [D$_6$]DMSO:CDCl$_3$=1:1, 30° C., TMS): δ=5.51 (s, 12H, CH); 5.27 (s, 12H, CH$_2$); 3.20 ppm (s, 36H, CH$_3$); $^{13}$C NMR (125 MHz, [D$_6$]DMSO:CDCl$_3$=1:1, 30° C., TMS): δ=159.7, 158.9, 68.3, 49.2, 31.47 ppm; m.p.>300° C. (dec.); HRMS (ESI⁻) m/z calcd for [C42H60N24O12+Cl⁻]: 1127.4506; found: 1127.4500.

Example 5

Tetraicosamethylbambus[12]uril (M2) (n=12; R1 and R2=O; R5, R6, R7, R8, R9, R10=H; R3, R4=methyl; for reaction scheme see FIG. 4)

2,4-dimethylglycoluril (3.0 g, 17 mmol) and paraformaldehyde (0.52 g, 17 mmol) were heated at 60° C. in the mixture of HCl (35%, 6 ml) and water (5 ml) for 48 h. The precipitate was removed by filtration and the filtrate was left standing at room temperature for 48 h. The resulting precipitate was collected by filtration. White powder was dissolved in mixture of methanol:chloroform=1:1 and purified using GPC (gel permeation chromatography). Yield 10%. $^1$H NMR (500 MHz, [D$_6$]DMSO:CDCl$_3$=1:1, 30° C., TMS): δ=5.21 (s, 24 H); 4.98 (s, 24 H); 3.01 (s, 72 H); HRMS (ESI–) m/z calcd for [C84H120N48O24+Cl⁻]: 2219.9328; found: 2219.9322.

Example 6

Dodecaethylbambus[6]uril (M3) (n=6; R1 and R2=O; R5, R6, R7, R8, R9, R10=H; R3, R4=ethyl; for reaction scheme see FIG. 4)

2,4-Diethylglycoluril (436 mg, 2.2 mmol), paraformaldehyde (67 mg, 2.2 mmol), HCl (35%, 0.75 ml), and H$_2$O (0.4 ml) were heated at 100° C. for 50 minutes and then cooled down at room temperature for 6 h. The resulting precipitate was collected by filtration, washed with 1M HCl and water, and dried under vacuum to give white solid in 16% yield.

HRMS (ESI⁻): m/z calcd for [C54H84N24O12+Cl⁻]: 1295.6383; found: 1295.6361.

Example 7

Dodecapropylbambus[6]uril (M4) (n=6; R1 and R2=O; R5, R6, R7, R8, R9, R10=H; R3, R4=propyl; for reaction scheme see FIG. 4)

2,4-Dipropylglycoluril (436 mg, 2.2 mmol), paraformaldehyde (67 mg, 2.2 mmol), HCl (35%, 0.75 ml), and H$_2$O (0.4 ml) were heated at 100° C. for 50 minutes and then cooled down at room temperature for 6 h. The resulting precipitate was collected by filtration, washed with 1M HCl and water, and dried under vacuum to give white solid in 21% yield.

HRMS (ESI⁻): m/z calcd for [C42H60N24O12+Cl⁻]: 1463.8261; found: 1463.8221.

Example 8

Tetraicosapropylbambus[12]uril (M5) (n=12; R1 and R2=O; R5, R6, R7, R8, R9, R10=H; R3, R4=propyl; for reaction scheme see FIG. 4)

2,4-propylglycoluril (500 mg, 2.2 mmol) and paraformaldehyde (67 mg, 2.2 mmol) were heated at 100° C. in the mixture of HCl (35%, 0.75 ml) and water (0.4 ml) for 50 minutes. The precipitate was removed by filtration and the filtrate was left at room temperature for 48 h. The resulting precipitate was collected by filtration. White powder was dissolved in mixture of methanol:chloroform=1:1 and purified using GPC (gel permeation chromatography). Yield 3%.

HRMS (ESI⁻): m/z calcd for [C132H216N48O24+Cl⁻]: 2892.6840; found: 2892.6865.

Example 9

Octabenzylbambus[4]uril (M6) (n=4; R1 and R2=O; R5, R6, R7, R8, R9, R10=H; R3, R4=benzyl; for reaction scheme see FIG. 4)

2,4-Dibenzylglycoluril (2.0 g, 6.2 mmol), paraformaldehyde (0.28 g, 9.3 mmol), p-toluenesulfonic acid (2.4 g), and tetramethyleneammonium fluoride (1 g) were heated at 100° C. in chloroform (100 ml) for 24 h. After reaction the solvent was evaporated and the resulting precipitate was washed with hot methanol. Yield 18%.

HRMS (ESI⁺): m/z calcd for [C76H72N16O8+H⁺]: 1337.5792; found: 1337.5771.

Example 10

Dodecabenzylbambus[6]uril (M7) (n=6; R1 and R2=O; R5, R6, R7, R8, R9, R10=H; R3, R4=benzyl; for reaction scheme see FIG. 4)

2,4-Dibenzylglycoluril (2.0 g, 6.2 mmol), paraformaldehyde (0.28 g, 9.3 mmol), p-toluenesulfonic acid (2.4 g), and tetramethyleneammonium fluoride (1 g) were heated at 100° C. in chloroform (100 ml) for 24 h. After reaction the solvent was evaporated and the resulting precipitate was stirred in hot methanol (200 ml). Remained solid was removed by filtration. The filtrate was concentrated by evaporation from 200 ml to 50 ml. The macrocycle was separated from the solution by slow evaporation of the solvent. Yield 20%.

HRMS (ESI⁺): m/z calcd for [C114H108N24O12+H⁺]: 2005.8651; found: 2005.8614

Example 11

Octabenzylthiobambus[4]uril (M8) (n=4; R1 and R2=S; R5, R6, R7, R8, R9, R10=H; R3, R4=benzyl; for reaction scheme see FIG. 4)

2,4-Dibenzylthioglycoluril (2.2 g, 6.2 mmol), paraformaldehyde (0.28 g, 9.3 mmol), p-toluenesulfonic acid (2.4 g), and tetramethyleneammonium fluoride (1 g) were heated at 100° C. in chloroform (100 ml) for 12 h. The reaction solution was cooled down slowly to yield the precipitate which was separated by filtration. Yield 5%.

HRMS (ESI⁺): m/z calcd for [C76H72N16O6S2+H⁺]: 1369.5335; found: 1369.5318.

Example 12

Dodecamethylbambus[6]uril (M1) (n=6; R1 and R2=O; R5, R6, R7, R8=H, R9, R10=CH$_2$OH; R3, R4=methyl; method of preparation without the use of carbonyl compound)

2,4-Di(hydroxymethyl)-6,8-dimethylglycoluril (9 g, 0.04 mol), HCl (35%, 18 ml), and $H_2O$ (12 ml) were stirred at room temperature for 24 h. The resulting precipitate was collected by filtration, washed with 1M HCl and water, and dried under vacuum to give white solid in 23% yield.

HRMS (ESI$^-$) m/z calcd for $[C_{42}H_{60}N_{24}O_{12}+Cl^-]$: 1127.4506; found: 1127.4496.

Example 13

Figure 5:
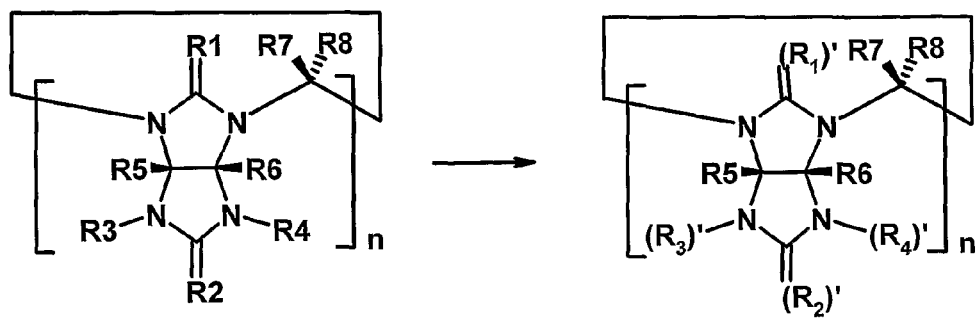
FIG. 5 shows the reaction scheme of the modification of the macrocyclic compounds of general formula I.

Octabenzylthiobambus[4]uril (M8) (n=4; R1 a R2=O; (R1)' a (R2)'=S, R5, R6, R7, R8, R9, R10=H; R3, R4, (R3)', (R4)'=benzyl; for reaction scheme see FIG. 5)

Octabenzylbambus[4]uril (M6) (0.2 g, 0.15 mmol) was dissolved in toluene (10 ml). Lawesson reagent (1.2 g) was added to the solution and the resulting solution was stirred under reflux for 3 h. The resulting precipitate was collected by filtration and washed with toluene Yield 55%.

HRMS (ESI$^+$): m/z calcd for $[C76H72N16O6S2+H^+]$: 1369.5335; found: 1369.5318.

Example 14

Bambus[4]uril (M9) (n=4; R1 and R2=O; R5, R6, R7, R8, R9, R10=H; R3, R4=benzyl, (R3)', (R4)'=H; for reaction scheme see FIG. 5)

Octabenzylbambus[4]uril (M6) (0.2 g, 0.15 mmol) and $(NH_4)_2Ce(NO_3)_6$ (2.0 g) were dissolved in the mixture of acetonitrile (20 ml) and water (5 ml). The solution was refluxed for 3 h. The resulting precipitate was collected by filtration and recrystallized from diluted HCl. Yield 25%.

HRMS (ESI$^+$): m/z calcd for $[C20H24N16O8+H^+]$: 617.2036; found: 617.2030

Example 15

Bambus[4]uril (M9) (n=4; R1, R2, (R1)', (R2)'=O; R5, R6, R7, R8, R9, R10=H; R3 and R4=benzyl, (R3)' and (R4)'=H; for reaction scheme see FIG. 5)

Suspension of octabenzylbambus[4]uril (M6) (0.1 g, 0.08 mmol) and 10% w/w Pd—C (0.1 g) in the mixture of methanol (10 ml) and ethyl acetate (50 ml) was stirred under hydrogen atmosphere, at atmospheric pressure and room temperature for 70 h. The solids were removed by filtration. The filtrate was evaporated and the obtained product was washed by methanol.

HRMS (ESI$^+$): m/z calcd for $[C20H24N16O8+H^+]$: 617.2036; found: 617.2035

Example 16

Dodecamethylbambus[6]uril-HI complex (0.5 g) was dissolved in the mixture of chloroform (50 ml) and methanol (50 ml). 30% $H_2O_2$ (0.25 ml) was added and the solution was stirred at room temperature for 24 h. The resulting white precipitate was collected by filtration and washed with equimolar mixture of chloroform and methanol. The obtained powder does not dissolve in any of studied solvent systems including chloroform, methanol, DMSO, acetonitrile, water or the mixtures of these solvents. When tetrabutylammonium bearing bromide, iodide, and tetrafluoroborate anions is added to the suspension of obtained white powder in equimolar mixture of chloroform and methanol the immediate formation of transparent solution was observed. $^1H$ NMR spectra of the solutions correspond to the spectra of the complex between dodecamethylbambus[6]uril and corresponding anion. This experiment showed that the obtained powder is anion free dodecamethylbambus[6]uril which dissolved in equimolar mixture of chloroform and methanol immediately after the formation of complex with the corresponding halide anion.

Example 17

Titanium dioxide powder (Aeroxide P25, typically 0.1 mg) was suspended in a solution of dodecamethylbambus[6]uril-HI complex (5.0 mM) in acetonitrile/water (1:1, 0.5 mL) in a standard quartz UV cuvette. The mixture was purged with oxygen for 5 min and irradiated at either wave lengths 254 or 366 nm. After 4 h white precipitated of anion free dodecamethylbambus[6]uril was obtained in 87% yield. The obtained powder does not dissolve in any of studied solvent systems including chloroform, methanol, DMSO, acetonitrile, water or the mixtures of these solvents. When tetrabutylammonium bearing bromide, iodide, and tetrafluoroborate anions is added to the suspension of obtained white powder in equimolar mixture of chloroform and methanol the immediate formation of transparent solution was observed. $^1H$ NMR spectra of the solutions correspond to the spectra of the complex between dodecamethylbambus[6]uril and corresponding anion. This experiment showed that the obtained powder is anion free dodecamethylbambus[6]uril which dissolved in equimolar mixture of chloroform and methanol immediately after the formation of complex with corresponding halide anion.

Example 18

Tetrabutylammonium iodide (150 mg) and dodecamethylbambus[6]uril-HCl complex were dissolved in the mixture of chloroform (1 ml) and methanol (1 ml). Single crystals suitable for X-ray crystallography were obtained after 2 days upon slow evaporation of the solvent. Determined crystal structure revealed the presence of inclusion complex in which iodide anion is bound in the centre of cavity of dodecamethylbambus[6]uril. One equivalent of tetrabutylammonium cation was also present in the crystal structure. The composition of the crystal as well as the presence of the complex was confirmed using $^1H$ NMR spectroscopy.

$^1H$ NMR ($CD_3OD:CDCl_3$ 2:1, 300 MHz); δ (ppm) 5.51 (s, 12 H); 5.01 (s, 12 H); 3.17 (t, 8 H); 3.12 (s, 36 H), 1.62 (m, 8 H); 1.39 (m, 8 H); 0.99 (t, 12 H).

Example 19

Tetrabutylammonium bromide (150 mg) and dodecamethylbambus[6]uril-HCl complex were dissolved in the mixture of chloroform (1 ml) and methanol (1 ml). Single crystals suitable for X-ray crystallography were obtained after 2 days upon slow evaporation of the solvent. Determined crystal structure revealed the presence of inclusion complex in which bromide anion is bound in the centre of cavity of dodecamethylbambus[6]uril. One equivalent of tetrabutylammonium cation was also present in the crystal structure. The composition of the crystal as well as the presence of the complex was confirmed using $^1H$ NMR spectroscopy.

$^1H$ NMR ($CD_3OD:CDCl_3$ 2:1, 300 MHz); δ (ppm) 5.47 (s, 12 H); 5.09 (s, 12 H); 3.17 (t, 8 H); 3.12 (s, 36 H), 1.62 (m, 8 H); 1.39 (m, 8 H); 0.99 (t, 12 H).

Example 20

Tetrabutylammonium tetrafluoroborate (150 mg) and dodecamethylbambus[6]uril-HCl complex were dissolved in the mixture of chloroform (1 ml) and methanol (1 ml). Single crystals suitable for X-ray crystallography were obtained after 2 days upon slow evaporation of the solvent. Determined crystal structure revealed the presence of inclusion complex in which tetrafluoroborate anion is bound in the centre of cavity of dodecamethylbambus[6]uril. One equivalent of tetrabutylammonium cation was also present in the crystal structure. The composition of the crystal as well as the presence of the complex was confirmed using $^1$H NMR spectroscopy.

$^1$H NMR (CD$_3$OD:CDCl$_3$ 2:1, 300 MHz); δ (ppm) 5.23 (s, 12 H); 4.97 (s, 12 H); 3.17 (t, 8 H); 3.06 (s, 36 H), 1.62 (m, 8 H); 1.39 (m, 8 H); 0.99 (t, 12 H).

Example 21

NaBr (0.5 g) and dodecamethylbambus[6]uril-HCl complex (0.5 g) were stirred in the mixture of chloroform (5 ml) and ethanol (5 ml). Undissolved inorganic salt was removed by the filtration. The evaporation of 5 ml of solvent resulted in precipitate which was collected by filtration. Obtained white powder of dodecamethylbambus[6]uril-bromide complex was confirmed using $^1$H NMR spectroscopy.

$^1$H NMR (CD$_3$OD:CDCl$_3$ 2:1, 300 MHz); δ (ppm) 5.47 (s, 12 H); 5.09 (s, 12 H); 3.12 (s, 36 H).

Example 22

NaI (0.5 g) and dodecamethylbambus[6]uril-HCl complex (0.5 g) were stirred in the mixture of chloroform (5 ml) and ethanol (5 ml). Undissolved inorganic salt was removed by the filtration. The evaporation of 5 ml of solvent resulted in precipitate which was collected by filtration. Obtained white powder of dodecamethylbambus[6]uril-iodide complex was confirmed using $^1$H NMR spectroscopy.

$^1$H NMR (CD$_3$OD:CDCl$_3$ 2:1, 300 MHz); δ (ppm) 5.51 (s, 12 H); 5.01 (s, 12 H); 3.12 (s, 36 H).

Example 23

NaBF$_4$ (0.5 g) and dodecamethylbambus[6]uril-HCl complex (0,5 g) were stirred in the mixture of chloroform (5 ml) and ethanol (5 ml). Undissolved inorganic salt was removed by the filtration. The evaporation of 5 ml of solvent resulted in precipitate which was collected by filtration. Obtained white powder of dodecamethylbambus[6]uril-tetrafluoroborate complex was confirmed using $^1$H NMR spectroscopy.

$^1$H NMR (CD$_3$OD:CDCl$_3$ 2:1, 300 MHz); δ (ppm) 5.23 (s, 12 H); 4.97 (s, 12 H); 3.06 (s, 36 H).

Example 24

Equimolar mixture of dodecamethylbambus[6]uril-HCl complex and tetrabutylammonium bearing bromide, iodide, and tetrafluoroborate anions was dissolved in the mixture of CD$_3$OD:CDCl$_3$=2:1 to obtain solution in which overall concentration of dissolved solids was 5 mM. In all cases obtained $^1$H NMR spectrum was identical with the spectrum of corresponding complex (see Example 20-22). As signals corresponding to dodecamethylbambus[6]uril-HCl complex were not observed the value of association constants for all complexes was calculated to be higher than $5\times10^4$ M$^{-1}$.

Example 25

Figure 6:
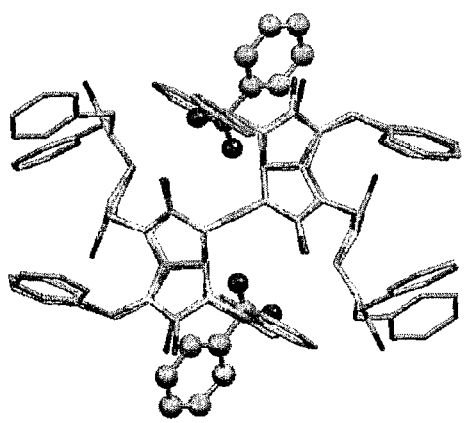
FIG. 6 shows the x-ray crystal structure of the complex between the macrocycle (M7) and two benzoate anions from Example 25. Hydrogen atoms and also solvent molecules and tetrabutylammonium canion were removed for clarity.

Dodecabenzylbambus[6]uril was dissolved in chloroform in the presence of three equivalents of tetrabuthylammonium benzoate. Single crystals suitable for X-ray crystallography were obtained after 1 day upon slow evaporation of the solvent. Determined crystal structure revealed the presence of the complex in which two benzoate anions interact with one macrocycle (FIG. 6). One equivalent of tetrabutylammonium cation was also present in the crystal structure.

Example 26

Figure 7:
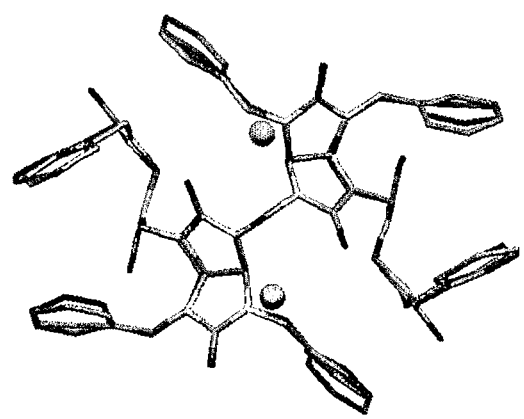
FIG. 7 shows the x-ray crystal structure of the complex between the macrocycle (M7) and two chloride anions from Example 26. Hydrogen atoms and also solvent molecules and tetrabutylammonium canion were removed for clarity.

Dodecabenzylbambus[6]uril was dissolved in chloroform in the presence of three equivalents of tetrabuthylammonium chloride. Single crystals suitable for X-ray crystallography were obtained after 1 day upon slow evaporation of the solvent. Determined crystal structure revealed the presence of the complex in which two chloride anions interact with one macrocycle (FIG. 7). One equivalent of tetrabutylammonium cation was also present in the crystal structure.

Example 27

Figure 8:
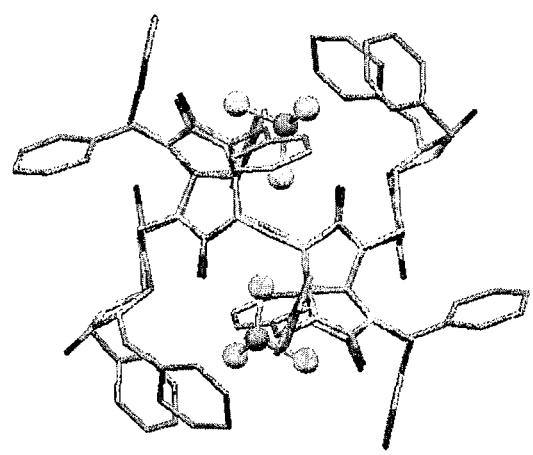
FIG. 8 shows the x-ray crystal structure of the complex between the macrocycle (M7) and two molecules of chloroform from Example 27. Hydrogen atoms and solvent molecules were removed for clarity.

Dodecabenzylbambus[6]uril was dissolved in chloroform. Single crystals suitable for X-ray crystallography were obtained after 1 day upon slow evaporation of the solvent. Determined crystal structure revealed the presence of the complex in which two molecules of the solvent are included within one macrocycle (FIG. 8).

Example 28

Solutions of dodecamethylbambus[6]uril and chloride salts of Na$^+$, K$^+$, and Cs$^+$ in the mixture CD$_3$CN:H$_2$O=1:1 were analyzed by ESI MS. In negative ion polarity ESI MS mode only one major peak corresponding to [dodecamethylbambus[6]uril-Cl$^-$] (m/z 1127.45) was detected. In positive ion polarity ESI MS mode the peaks corresponding to [dodecamethylbambus[6]uril-Na$^+$] (m/z 1115.47), [dodecamethylbambus[6]uril-K$^+$] (m/z 1131.45), and [dodecamethylbambus[6]uril-Cs$^+$] (m/z 1225.39) were detected as dominant signals. The intensity of the peaks for the complexes between the macrocycle and cations decrease in following order: Cs$^+$>K$^+$>Na$^+$.

Industrial Applicability

New macrocyclic compounds of the general formula I may be used for water purification, desalination, removing of various compounds from the solution, separation of liquid mixtures, and mixtures of gases and organic solvent vapors, preparation of ion-exchange materials and materials which are used as stationary phase in chromatography, construction of sensors, transporting and targeting of drugs in organisms, and also preparation of material bearing aromatic or curative compounds.

The invention claimed is:
1. Macrocyclic compounds of formula I

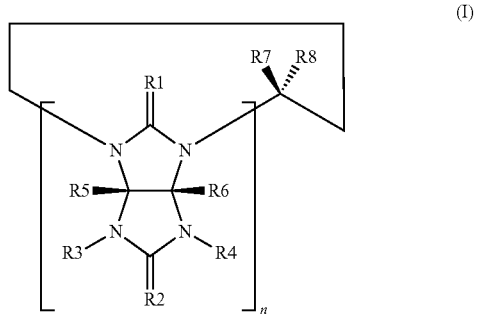

wherein n is an integer in the range of 4 to 24,

R1 and R2 are each independently O or S,

R3, R4, R7, R8 are each selected independently from the group consisting of hydrogen atom, alkyl, alkenyl, alkynyl, cycloalkyl, cycloalkenyl, aryl, and heteroaryl, R5, R6 are each selected independently from the group consisting of hydrogen atom, —OH, —COOH, —NH$_2$, —NO$_2$, —NHNH$_2$, nitrile, alkyl, alkenyl, alkynyl, cycloalkyl, cycloalkenyl, alkoxy, hydrocarbylthio, hydrocarbylamino, dihydrocarbylamino, carboxyl, aryl, and heteroaryl, wherein halogen is selected from the group consisting of fluorine, chlorine, bromine and iodine, alkyl is a linear or branched alkyl chain having 1 to 30 carbon atoms, and in which any of the —CH$_2$— groups can be replaced by —O—, —S— or —NH— group, while the alkyl can be unsubstituted or substituted by 1 to 5 groups selected from the group consisting of —OH, —SH, =O, halogen, aryl, —NH$_2$ and —COOR$^c$, where R$^c$ is hydrogen atom or alkyl group having 1 to 6 carbon atoms, alkenyl is linear or branched chain containing 2 to 30 carbon atoms, and containing at least one double bond, and in which any of the —CH$_2$— groups can be replaced by —O—, —S— or —NH— group, and any =CH— group can be replaced by =N—, while the alkenyl can be unsubstituted or substituted by 1 to 5 groups selected from the group consisting of —OH, —SH, =O, halogen, aryl, —NH$_2$, and —COOR$^c$, wherein R$^c$ is hydrogen atom or alkyl group having 1 to 6 carbon atoms, alkynyl is linear or branched chain having 2 to 30 carbon atoms, and containing at least one triple bond, and which may contain also a double bond, in this alkynyl chain any of the —CH$_2$— groups can be replaced by —O—, —S— or —NH— group, and any =CH— group can be replaced by =N—, while the alkynyl can be unsubstituted or substituted by 1 to 5 groups selected from the group consisting of —OH, —SH, =O, halogen, aryl, —NH$_2$, and —COOR$^c$, wherein R$^c$ is hydrogen atom or alkyl group having 1 to 6 carbon atoms, cycloalkyl is linear or branched group having 4 to 10 carbon atoms, and containing at least one cycle, in which any of the —CH$_2$— groups can be replaced by —O—, —S— or —NH— group, while the cycloalkyl can be unsubstituted or substituted by 1 to 5 groups consisting of —OH, —SH, =O, halogen, aryl, —NH$_2$, and —COOR$^c$, wherein R$^c$ is hydrogen atom or alkyl group having 1 to 6 carbon atoms, cycloalkenyl is linear or branched group having 4 to 10 carbon atoms, and containing at least one double bond and at least one cycle, in which any of the —CH$_2$— groups can be replaced by —O—, —S— or —NH— group, and any =CH— group can be replaced by =N—, while the cycloalkenyl can be unsubstituted or substituted by 1 to 5 groups consisting of —OH, —SH, =O, halogen, aryl, —NH$_2$, and —COOR$^c$, where R$^c$ is hydrogen atom or alkyl group having 1 to 6 carbon atoms, alkoxy is a group —OR$^a$, where R$^a$ is selected from the group consisting of alkyl, alkenyl, alkynyl, cycloalkyl, and cycloalkenyl, hydrocarbylthio is a group —SR$^a$, where R$^a$ is selected from the group consisting of alkyl, alkenyl, alkynyl, cycloalkyl, and cycloalkenyl, hydrocarbylamino is a group —NHR$^a$, where R$^a$ is selected from the group consisting of alkyl, alkenyl, alkynyl, cycloalkyl, and cycloalkenyl, dihydrocarbylamino is a group —NR$^a$R$^b$, where R$^a$ and R$^b$ are each independently selected from the group consisting of alkyl, alkenyl, alkynyl, cycloalkyl, and cycloalkenyl, carboxyl is a group —COOR$^a$, where R$^a$ is selected from the group consisting of alkyl, alkenyl, alkynyl, cycloalkyl, and cycloalkenyl, aryl is a hydrocarbon group having 6 to 30 carbon atoms, and containing at least one aromatic ring, and the aryl can be unsubstituted or substituted by 1 to 5 groups selected independently from the group consisting of —OH, —SH, =O, halogen, —NH$_2$, and —COOR$^c$, where R$^c$ is hydrogen atom or alkyl group having 1 to 6 carbon atoms, heteroaryl is a hydrocarbon group having 4 to 30 carbon atoms, and containing at least one aromatic ring, containing at least one heteroatom selected from the group comprising O, S, N, and the heteroaryl can be unsubstituted or substituted by 1 to 5 groups selected independently from —OH, —SH, =O, halogen, —NH$_2$, and —COOR$^c$, where R$^c$ is hydrogen atom or alkyl group having 1 to 6 carbon atoms.

2. A method of preparation of the macrocyclic compounds of general formula I of claim 1, characterized in that a compound of formula II

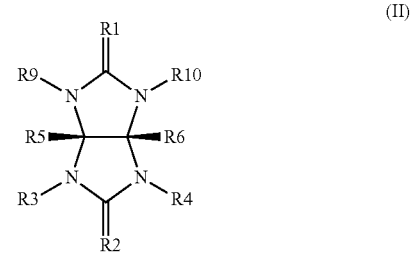

(II)

wherein

R1, R2 are independently O or S,

R3, R4 are each selected independently from the group consisting of alkyl, alkenyl, alkynyl, cycloalkyl, cycloalkenyl, aryl, and heteroaryl, R5 and R6 are each selected independently from the group consisting of hydrogen atom, —OH, —COOH, —NH$_2$, —NO$_2$, —NHNH$_2$, nitrile, alkyl, alkenyl, alkynyl, cycloalkyl, cycloalkenyl, alkoxy, hydrocarbylthio, hydrocarbylamino, dihydrocarbylamino, carboxyl, aryl, and heteroaryl, R9 and R10 are each independently selected from the group consisting of —H, —Cl, —Br, —I, —CH$_2$OH, —CO-alkyl, —CO-aryl, —CH$_2$O-alkyl, —CH$_2$O-aryl, is reacted with a compound of formula III or IV,

(III)

(IV)

wherein
R7 and R8 are each selected independently from the group consisting of hydrogen atom, alkyl, alkenyl, alkynyl, cycloalkyl, cycloalkenyl, aryl, and heteroaryl, and
m is an integer in the range of from 4 to 20,
in the presence of an acid.

3. A method of removing one or more substances from a liquid comprising treating the liquid with a macrocyclic compound of formula I according to claim 1, and binding the substances to be removed with said macrocyclic compound of formula I.

4. The method of claim 3, wherein the liquid is water and the method is used to purify the water.

5. The method of claim 4, wherein the method is used to desalinate the water.

6. The method of claim 4, wherein the liquid being treated is waste water.

7. The method of claim 3, wherein macrocyclic compound of formula I is incorporated into a polymeric membrane and the polymeric membrane is used in treating the liquid.

8. The method of claim 7, wherein the polymeric membrane comprising macrocyclic compound of formula I is used for at least one of separation of liquid mixtures, and separating mixtures of gases and organic solvent vapors.

9. The method of claim 3, wherein the liquid is treated with macrocyclic compound of formula I in powder form.

10. The method of claim 3, wherein macrocyclic compound of formula I is attached to a support material, and the resulting material is used as stationary phase in chromatography.

11. The method of claim 3, wherein at least one of R1 and R2 of the macrocyclic compound of formula I is S, and wherein macrocyclic compound of formula I is attached to a metal surface.

12. The method of claim 3, wherein the substance bound to the compound of formula I is selectively removed from the macrocycle.

13. The method of claim 3, wherein the macrocyclic compound of formula I functions as an ion exchange material.

14. The macrocyclic compounds of claim 1, wherein at least one of R1 and R2 is S.

15. The macrocyclic compounds of claim 1, wherein at least one of R7 and R8 is selected from the group consisting of
alkyl, alkenyl, alkynyl, cycloalkyl, cycloalkenyl, aryl, and heteroaryl.

16. The macrocyclic compounds of claim 1, wherein R3 and R4 are selected from the group consisting of hydrogen atom, alkyl, alkynyl, cycloalkyl, aryl, and heteroaryl.

* * * * *

UNITED STATES PATENT AND TRADEMARK OFFICE
CERTIFICATE OF CORRECTION

Page 1 of 2

PATENT NO. : 8,779,120 B2
APPLICATION NO. : 13/265432
DATED : July 15, 2014
INVENTOR(S) : Vladimir Sindelar, Jan Svec and Vaclav Havel It is certified that error appears in the above-identified patent and that said Letters Patent is hereby corrected as shown below:

Delete Title Page, and replace with new Title Page. (attached)

In the Claims

The image of formula (I) in claim 1 at column 14, lines 55-65 is hereby changed to:

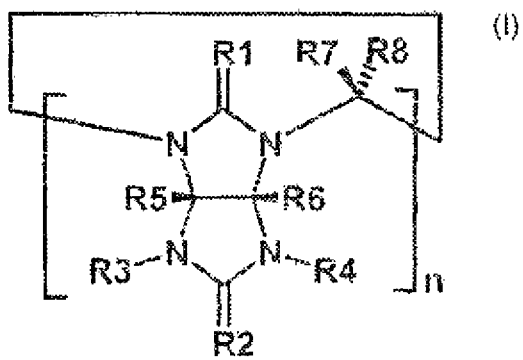

Signed and Sealed this
Seventh Day of October, 2014

Michelle K. Lee
*Deputy Director of the United States Patent and Trademark Office*

(12) United States Patent
Sindelar et al.

(10) Patent No.: US 8,779,120 B2
(45) Date of Patent: Jul. 15, 2014

(54) MACROCYCLIC DERIVATIVES OF GLYCOLURILS, AND METHODS OF PREPARING AND USING THE SAME

(75) Inventors: Vladimir Sindelar, Veverske Kninice (CZ); Jan Svec, Cerveny Kostelec (CZ); Vaclav Havel, Opava (CZ)

(73) Assignee: Masarykova Univerzita, Brno (CZ)

( * ) Notice: Subject to any disclaimer, the term of this patent is extended or adjusted under 35 U.S.C. 154(b) by 132 days.

(21) Appl. No.: 13/265,432

(22) PCT Filed: Oct. 26, 2010

(86) PCT No.: PCT/CZ2010/000110
§ 371 (c)(1),
(2), (4) Date: Oct. 20, 2011

(87) PCT Pub. No.: WO2011/057590
PCT Pub. Date: May 19, 2011

(65) Prior Publication Data
US 2012/0041192 A1 Feb. 16, 2012

(30) Foreign Application Priority Data
Nov. 16, 2009 (CZ) .......................... PV 2009-761

(51) Int. Cl.
C07D 487/22 (2006.01)
C07D 487/14 (2006.01)

(52) U.S. Cl.
CPC .......... C07D 487/14 (2013.01); C07D 487/22 (2013.01)
USPC .......................................... 540/460; 548/303.4

(58) Field of Classification Search
USPC .......................................... 548/303.4; 540/460
See application file for complete search history.

(56) References Cited

U.S. PATENT DOCUMENTS 5,298,539 A 3/1994 Singh et al.

FOREIGN PATENT DOCUMENTS

| EP | 366884 A2 * | 5/1990 |
| EP | 1094065 | 4/2001 |
| WO | WO0068232 | 11/2000 |
| WO | WO2007106144 | 9/2007 |

OTHER PUBLICATIONS

Svec et al., Angewandte Chemie, International Edition (published online Mar. 9, 2010), 49(13), pp. 2378-2381.*
Lagona, J., et al., "The Cucurbit[n]uril Family", Angewandte Chemie, Int'l Edition, Wiley-Vch Verlag Gmbh & Co., Weinheim, vol. 44, No. 31, Aug. 5, 2005, pp. 4844-4870.
Svec, J., et al., "Bambus[6]uril**", Angewandte Chemie, Wiley-Vch Verlag GmbH & Co., Weinheim, vol. 122, No. 13, Mar. 9, 2010, pp. 2428-2431.
Freeman, W.A. et al., "Cucurbituril", J. Am. Chem. Soc. 1981, 103, 7367-7368.
Huang, Wei-Hao, et al., "Chiral Recognition inside a Chiral Cucurbituril**", Angew. Chem., Int. Ed. 2007, 46, 7425-7427.
Huang, Wei-Hao, et al., "Nor-Seco-Cucurbit[10]uril Exhibits Homotropic Allosterism", J. Am. soc 2006, 128, 14744-14745.
Isaacs, L., et al., "The Inverted Cucurbit[n]uril Family", J. Am Chem. Soc. 2005, 127, 18000-18001.
Kim, Jaheon, et al., "New Cucurbituril Homologues: Syntheses, Isolation, Characterization, and X-ray Crystal Structures . . .", J. Am. Chem. Soc. 2000, 122, 540-541.
Lagona, Jason et al., "The Cucurbit[n]uril Family", Angew. Chem., Int. Ed. 2005, 44, 4844-4870.
Miyahara, Yuji et al., "Remarkably Facile Ring-Size Control in Macrocyclization: Synthesis of Hemicucurbit[6]uril and . . .", Angew. Chem., Int. Ed. 2004, 43, 5019-5022.
Rebek, Julius, Jr., "Reversible Encapsultion and Its Consequences in Solution", Acc. Chem. Res. 1999, 32, 278-286.
Rowan, A.E., et al., "Molecular and Supramolecular Objects from Glycoluril", Acc. Chem. Res. 1999, 32, 995-1006.

* cited by examiner

Primary Examiner — Laura L. Stockton
(74) Attorney, Agent, or Firm — Notaro, Michalos & Zaccaria P.C.

(57) ABSTRACT

The present invention relates to novel macrocyclic derivatives of glycolurils of general formula I, and methods of their preparation. These novel derivatives can be used for the selective removing of various compounds from solutions in polar and nonpolar solvents, and from water, e.g. for water purification and desalination, also for separation of liquid mixtures and mixtures of gases and organic solvent vapors, preparation of ion-exchange materials and materials which are used as stationary phase in chromatography, construction of sensors, transport and targeting of drugs in organisms, and also preparation of materials bearing aromatic or curative compounds.

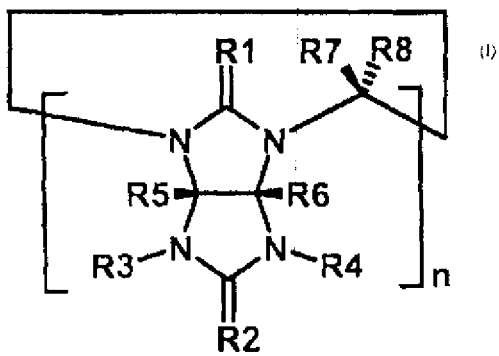

16 Claims, 4 Drawing Sheets